(12) United States Patent
Okazaki et al.

(10) Patent No.: US 7,541,490 B2
(45) Date of Patent: Jun. 2, 2009

(54) METHOD FOR PRODUCTION OF ACRYLIC ACID AND APPARATUS FOR PRODUCTION OF ACRYLIC ACID

(75) Inventors: Kazuto Okazaki, Himeji (JP); Yukihiro Matsumoto, Kobe (JP); Kazuhiko Sakamoto, Himeji (JP); Osamu Dodo, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 221 days.

(21) Appl. No.: 11/601,417

(22) Filed: Nov. 17, 2006

(65) Prior Publication Data

US 2007/0066845 A1 Mar. 22, 2007

Related U.S. Application Data

(62) Division of application No. 09/705,661, filed on Nov. 3, 2000, now Pat. No. 7,198,766.

(30) Foreign Application Priority Data

Nov. 5, 1999 (JP) .................... 11-315914

(51) Int. Cl.
*C07C 51/16* (2006.01)
*C07C 51/235* (2006.01)

(52) U.S. Cl. ...................... 562/532; 562/545

(58) Field of Classification Search ................. 562/600, 562/545, 532
See application file for complete search history.

(56) References Cited

U.S. PATENT DOCUMENTS

| 4,222,965 A | 9/1980 | Gorbunov et al. ............ 568/461 |
| 4,586,344 A | 5/1986 | Lutz et al. ..................... 62/101 |
| 4,769,998 A | 9/1988 | Oswalt et al. .................. 62/92 |

FOREIGN PATENT DOCUMENTS

| DE | 3836061 A | 6/1989 |
| DE | 4132097 A | 11/1992 |
| WO | WO 96/19922 | 7/1996 |

*Primary Examiner*—Taylor Victor Oh
(74) *Attorney, Agent, or Firm*—Porzio, Bromberg & Newman, P.C.

(57) ABSTRACT

Chilled coolant is prepared by liquid coolant utilizing the latent heat generated by a gasification of liquefied propylene, for example, and this chilled coolant is used in heat exchangers which are used in a process for production of acrylic acid or acrolein. This method allows effective utilization of the latent heat which used to be discarded and permits a reduction of energy consumption of cooling required separately in the step for production. By recovering the chilled coolant with the liquid coolant, it makes possible to stabilize the gasification of propylene, etc. and consequently stabilize the production of acrylic acid. This invention consists of providing the method for the production of acrylic acid, etc. and the apparatus which make effective use of the latent heat generated in the steps of production.

7 Claims, 3 Drawing Sheets

METHOD FOR PRODUCTION OF ACRYLIC ACID AND APPARATUS FOR PRODUCTION OF ACRYLIC ACID

CROSS-REFERENCE TO RELATED APPLICATION

This application is a divisional of U.S. patent application Ser. No. 09/705,661 filed Nov. 3, 2000 now U.S. Pat. No. 7,198,766 hereby incorporated in its entirety by reference into this application.

BACKGROUND OF THE INVENTION

1. Field of the Invention

This invention relates to a method for the production of acrylic acid, for example, which method comprises preparing the chilled coolant by utilizing the latent heat generated during the gasification of propylene and/or propane as the raw material for the production of acrylic acid and circulating the chilled coolant to the heat exchangers being used in the apparatus for the production of acrylic acid, and to the apparatus for the production of acrylic acid which is suitable for the method mentioned above.

2. Description of Related Art

Acrylic esters have been finding utility as materials for acrylic fiber copolymers, as emulsions for tackifiers and adhesives, and as raw materials for paints, processed fibers, leather products, and buildings. They have been consequently enjoying growing demands. In the circumstance, the desirability of developing a process which allows use of inexpensive raw materials, permits mass production, and restrains any addition to the environmental pollution has been finding popular recognition. The acrylic acid and the like which are used as raw materials for such acrylic esters are now produced by the reaction of catalytic gas phase oxidation of propylene, for example.

An example of the process for producing acrylic acid by this reaction of catalytic gas phase oxidation will be explained with the aid of FIG. 1 depicting the flow of the raw material for acrylic acid with thick lines and the flow of cooling water with thin lines.

First, the reaction of catalytic gas phase oxidation requires supply of the raw material therefore in the form of the gas as aptly implied by the name. A liquefied propylene 14 is gasified through the propylene evaporator 3, gaseous propylene from the evaporator is mixed with air 16 for use in the reaction of oxidation, and the resultant mixture is subsequently supplied to the reactor 4. When propylene, for example, is subjected to catalytic gas phase oxidation with the molecular oxygen-containing gas in the presence of the catalyst for the reaction of catalytic gas phase oxidation, the mixed gas containing such by-products as acetic acid in addition to acrylic acid, i.e. the product aimed at is obtained as the reaction product. The reaction product gas formed by the reaction of catalytic gas phase oxidation, therefore, is introduced into the acrylic acid absorbing column 5 and exposed therein to the acrylic acid absorbing solvent, thereby cooled and absorbed, and eventually the liquid containing acrylic acid and such by-products as acetic acid as well is obtained. Then, the solvent in this liquid is separated in the solvent separating column 6 and subsequently distilled and purified in the refining column 7 to separate acrylic acid 18 from by-product containing liquid and obtain the product aimed at.

In this case, a part of the bottom liquid in the acrylic acid absorbing column 5 is introduced into the circulation cooler 9 attached to the acrylic acid absorbing column and cooled by exchanging heat with the liquid coolant supplied from a part of liquid coolant supplying system 1 and then circulated to the acrylic acid absorbing column 5. Incidentally, the acrylic acid absorbing column 5 is generally installed with the absorbing solvent cooler 8 adapted to cool the acrylic acid absorbing solvent 21 for the purpose of enhancing the efficiency of acrylic acid absorption. The distillate from the top of the solvent separating column 6 is condensed in the condenser 10 attached to the solvent separating column 6 with the liquid coolant supplied from a part of the liquid coolant supplying system 1, thereby recovering the solvent 22. Similarly, the distillate from the top of the refining column 7 is condensed in the condenser 11 attached to the refining column 7 with the liquid coolant supplied from a part of the liquid coolant supplying system 1, thereby obtaining the acrylic acid 18. The liquid coolant resulting from heat exchange can be supplied to the methacrylic acid and/or (meth)acrylic esters plant 12, subjected to heat exchange therein, and then put to use. In any event, the liquid coolant lines are provided for the purpose of allowing circulation of this liquid coolant from these heat exchangers to the liquid coolant supplying system 1. Incidentally, the acrylic acid absorbing column 5 discharges the waste gas 20 through the top thereof.

It has been heretofore customary to supply steam 17 controlled by the pressure controller 24 to the evaporator 3 for the purpose of utilizing the high energy of the steam 17, thereby gasifying liquefied propylene. The condensed drain of the steam 17 resulting from the heat exchange has been utilized as the boiler feed water for the purpose of harnessing the sensible heat thereof.

This method, however, is at a disadvantage in suffering even a slight fluctuation of the steam pressure or the amount of supplied steam 17 to render the vapor pressure and the dryness of the propylene gas unstable because the energy of steam is high. In the production of acrylic acid by the reaction of catalytic gas phase oxidation, therefore, the composition of the reactant gas tends to vary and the stability of there action system itself tends to lose stability. Further, the concentration of the acrylic acid in the gas supplied to the acrylic acid absorbing column 5 likewise varies and, as a result, polymerization and clogging will happen at the column inside, and the efficiency of absorption will drop in the consequence of the formation of polymer. The decline of the efficiency of absorption lowers the concentration of the acrylic acid in the liquid in which acrylic acid is absorbed emanating from the acrylic acid absorbing column, with the result that the load on the column will rise during the separation of the solvent by the solvent separating column 6.

In the production of the acrylic acid, the acrylic acid absorbing column 5, the solvent separating column 6, the refining column 7, etc. are provided for the purpose of purifying the acrylic acid obtained by the reaction of catalytic gas phase oxidation and these columns are each provided with numerous heat exchangers adapted to enhance the efficiencies of absorption, separation, and purification by utilizing the principle of heat exchange. As concrete examples of the heat exchanger of this nature, the acrylic acid absorbing solvent cooler 8, the condenser 11 attached to the refining column 7, and the condenser 10 attached to the solvent separating column 6 may be installed. The cooling water for use in these heat exchangers is supplied from the liquid coolant supplying system 1 such as a refrigerator and/or cooling tower. Since the temperature of the cooling water varies due to the season, there are cases where the capacity for heat exchange will drop as the rise of cooling water temperature. To prevent this temperature from rising, another electric power is required for cooling the liquid coolant.

Further, in the case of the solvent separating column 6, for example, the distillate from the top of this column is condensed and cooled by the condenser 10 attached to the solvent separating column. If the efficiency of absorption in the acrylic acid absorbing column 5 falls down, the load exerted to bear on the subsequent solvent separating column 6 will be possibly elevated and the load on the condenser 10 will be consequently elevated. Owing to this rise of load coupled with the fall of the capacity for heat exchange due to the rise of the temperature of the cooling water mentioned above, the distillate from the top of the solvent separating column 6 will not be condensed or cooled sufficiently. Further, the distillate contains acrylic acid, polymerizable by-products, etc. besides the solvent. The solvent separating column 6 is usually operated under vacuum pressure. Under these complex circumstances, insufficient condensation of the distillate will possibly induce such problems as increasing the amount of the polymerizable materials to be scattered in the vacuum equipment connected to the condenser, and cause the vacuum equipment and the piping installed thereto to incur such adverse situation as polymerization and clogging. As a result, it possibly becomes difficult or even impossible to control the operating pressure of the column. Further, these detriments possibly induce the polymerization in the solvent separating column and give rise to such troubles as deterioration of final product quality.

Heretofore, the problem of the polymer formation due to the supply of the steam 17 thereto has been coped with only by periodic removal of the polymer deposited thereon.

SUMMARY OF THE INVENTION

The present inventor has elaborately studied the process for producing acrylic acid and consequently found that by substituting the liquid coolant for the steam 17 supplied as the heat source for gasifying propylene in the propylene evaporator, it is made possible to allow the reactant gas to be supplied stably and, at the same time, enable the total system for producing acrylic acid to be stabilized drastically, reduce the polymerization and clogging, what is more, allow the electric power heretofore required for the cooler to be decreased by utilizing the chilled coolant obtained during the gasification mentioned above. This invention has been perfected based on this discovery.

To be specific, the tasks imposed on this invention are accomplished by the following items (1) and (2).

(1) A method for the production of acrylic acid or acrolein, characterized by gasifying liquefied propylene and/or propane introduced into an evaporator by supplying a liquid coolant to the evaporator and, at the same time, preparing a chilled coolant by recovering the latent heat of the liquefied propylene and/or propane, subjecting the resultant gasified propane and/or propylene to a catalytic gas phase oxidation reaction thereby preparing a gas containing acrylic acid or acrolein, and using said chilled coolant in heat exchangers attached to the apparatus for the production acrylic acid or acrolein.

(2) An apparatus for the production of acrylic acid or acrolein, comprising means for gasifying liquefied propylene and/or propane introduced into an evaporator by supplying a liquid coolant to said evaporator and, at the same time, preparing a chilled coolant by recovering the latent heat of the liquefied propylene and/or propane, means for subjecting the resultant gasified propylene and/or propane to a catalytic gas phase oxidation reaction thereby preparing a gas containing acrylic acid or acrolein, and means for using said chilled coolant in heat exchangers attached to the apparatus for the production of acrylic acid or acrolein.

According to this invention, since the latent heat is recovered by liquid coolant, the gasification of propylene and/or propane can be effected stably and the supply of the reactor with propylene can be attained stably as compared with the conventional method utilizing steam. As a result, the absorption and the distillation in the acrylic acid absorbing column, solvent separating column, refining column, etc. can be stabilized and the final product can be improved in quality. At the same time, by using the chilled water prepared by the method mentioned above in the heat exchangers in the process of acrylic acid production, it is made possible to decrease the energy consumption for cooling.

DESCRIPTION OF THE PREFERRED EMBODIMENTS

Figure 1:
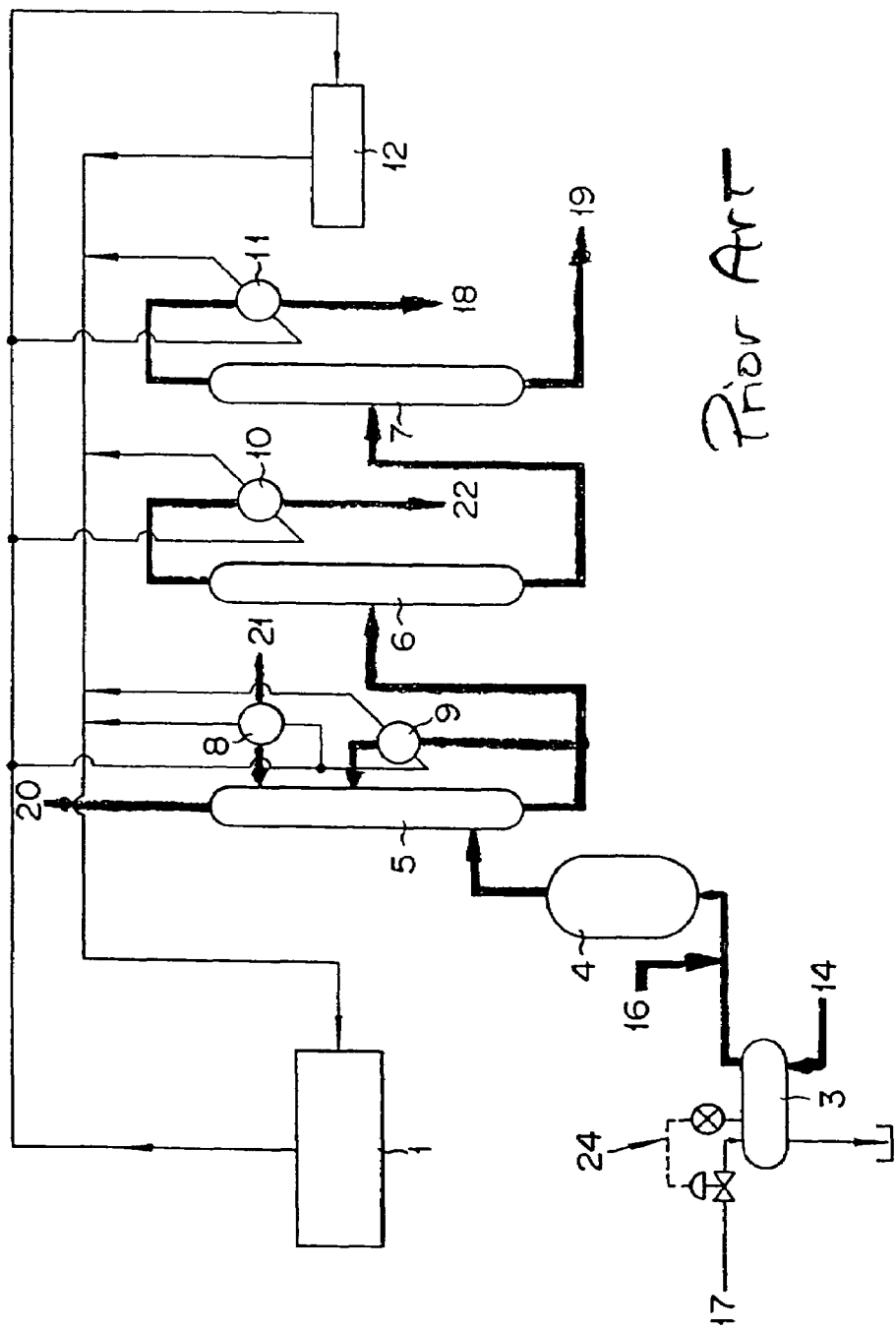
FIG. 1 is a diagram illustrating an example of the conventional process for production of acrylic acid by the reaction of catalytic gas phase oxidation, with the flows of raw materials for acrylic acid indicated in thick lines and those of cooling water in thin lines.

The first aspect of this invention consists in a method for the production of acrylic acid or acrolein, characterized by gasifying liquefied propylene and/or propane introduced into an evaporator by supplying a liquid coolant to the evaporator and, at the same time, preparing a chilled coolant by recovering the latent heat of the liquefied propylene and/or propane, subjecting the resultant gasified propane and/or propylene to a catalytic gas phase oxidation reaction thereby preparing a gas containing acrylic acid or acrolein, and using said chilled coolant in heat exchangers attached to the apparatus for the production acrylic acid or acrolein.

It has been heretofore customary to use steam 17 in gasifying liquefied propylene and/or propane. Since the steam has high energy, even a slight fluctuation of its pressure or supplied amount varies the composition of the reactant gas supplied to the reactor for catalytic gas phase oxidation and deprives the catalytic gas phase oxidation reaction itself of its stability. This invention, however, is enabled by using the liquid coolant in the place of the steam 17 to stabilize the gasification itself and also stabilize the whole reaction system and the whole of the subsequent steps for producing acrylic acid as well. The drain resulting from the use of steam 17 has been heretofore reused barely as the boiler feed water for the purpose of utilizing sensitive heat. Owing to the use of the liquid coolant, however, this invention enables the chilled coolant to be obtained in a large amount in consequence of the gasification and allows the reduction of the electric power consumed in the heat exchangers in the acrylic acid process by using the obtained chilled coolant. The term "liquid coolant" as used in this invention refers to the cooling agent which is used in gasifying the liquefied propylene and/or propane destined to serve as the raw material for the production of acrylic acid or acrolein. This liquid coolant is only required to retain a liquid state while it is supplied to the evaporator 3 and is allowed to be gasified or solidified while it is circulated to other heat exchangers or after it has been used therein. The term "chilled coolant" refers to the liquid coolant mentioned above which has exchanged heat with the liquefied propylene and/or propane and consequently has lower temperature than that of before heat exchange. In this invention, since the chilled coolant is circulated to and used in the heat exchangers, it is subject to change of heat and has the temperature thereof inevitably rise after exchange the heat in the heat exchangers. Even in this case, the chilled coolant is expressed so for the sake of convenience. When the chilled coolant is cyclically used as in the steps for production of acrylic acid, therefore, this chilled coolant is supplied to the evaporator after it has recovered heat. When the chilled coolant is in the liquid state in the evaporator, it answers the expression "liquid coolant" as defined in this specification. The expression "the heat transfer medium for the circulation in the reactor" which will be used hereinafter refers to the heat medium being circulated in the shell of the reactor for the catalytic gas phase oxidation reaction.

Figure 2:
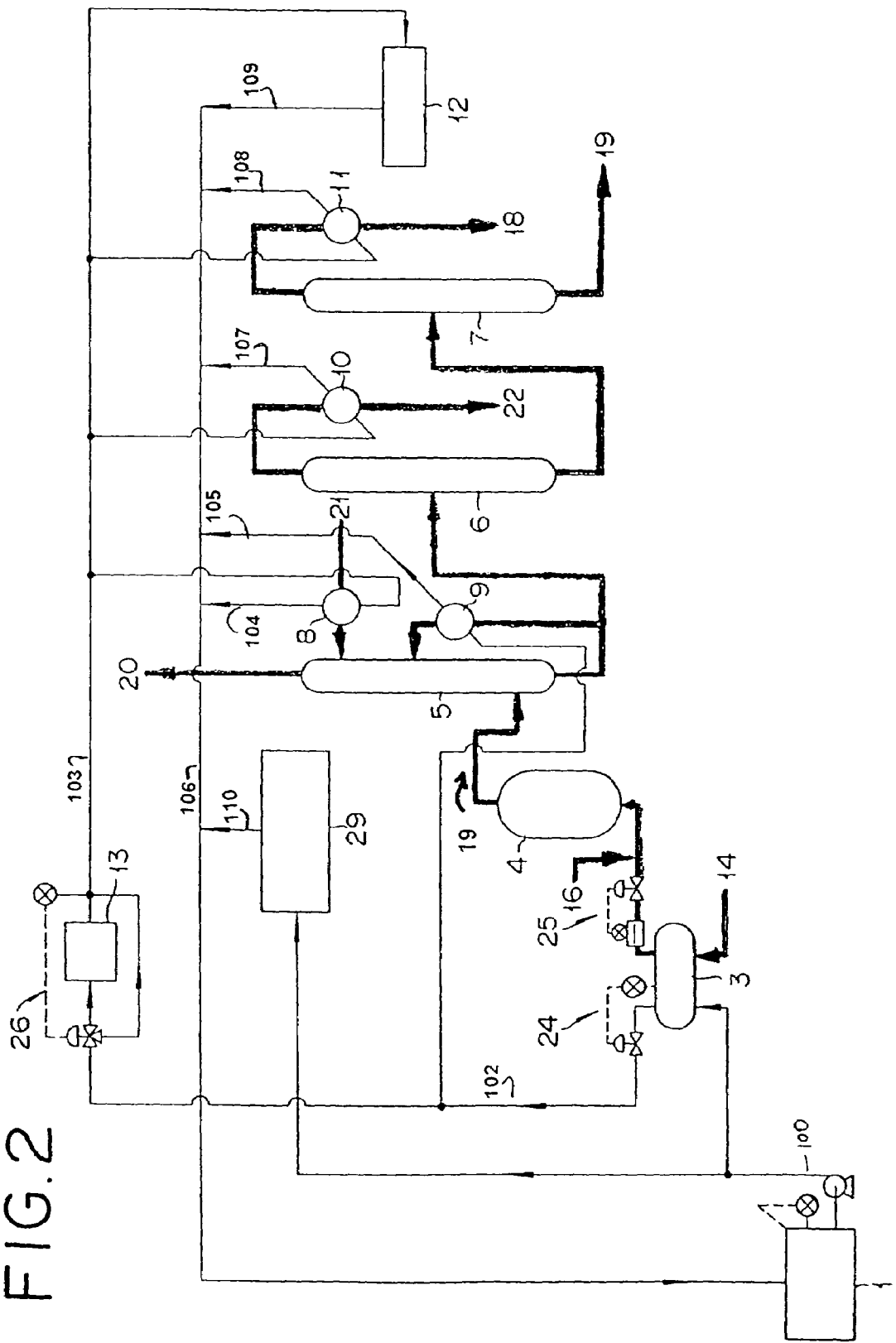
FIG. 2 is a diagram illustrating a preferred working example of this invention for producing acrylic acid by a two-step reaction using water as the liquid coolant and propylene as the raw material.

Now, as one example of the preferred embodiment of this invention, the production of acrylic acid by the two-step catalytic reaction using water as the liquid coolant and propylene as the raw material will be described with reference to FIG. 2. In FIG. 2 and in FIG. 3 as well which will be used hereinafter, the flows of the raw material for acrylic acid and lines for producing acrylic acid are indicated in thick lines and the flows of liquid coolant and chilled coolant in thin lines.

For a start, the liquid coolant supplied from the liquid coolant supplying system 1 is introduced to the propylene evaporator 3 via line L1 to gasify the liquefied propylene. The evaporator 3 is connected with the piping for introducing the liquid propylene and has empty space for introducing the liquid coolant, and enables gasification of liquefied propylene by the principle of heat exchanger, with the result that the liquid coolant will be converted into the chilled coolant.

As the liquid coolant, water or brine may be used. As the water, industrial water, city water, or other water may be used. The brine is known in numerous types such as ethylene glycol, methanol, and other aqueous solutions. This invention allows use of the brine as the known liquid coolant to be circulated to the heat exchangers. The brine is at an advantage in retaining the liquid state at lower temperature than water and allowing the lowest temperature for the liquid state to be adjusted in accordance with the composition thereof. The choice of water or brain as the liquid coolant and the question as to the kind of composition for the brine to be used may be properly decided to suit the kind of use and the purpose of use.

The method for production according to this invention has no particular restriction for the temperature of the liquid coolant to be supplied to the evaporator 3. This is because the liquid coolant is capable of stabilizing the reaction system and reducing the power for cooling so long as it is in a liquid state at the time that it is introduced into the evaporator 3. In the gasification of the liquefied propylene and/or propane, the temperature is in the range of 0-50° C., preferably 5-40° C., and particularly preferably 5-35° C. The reason for this range of temperature will be described in detail below.

First, the vaporizing temperature of the liquefied propylene 14 in the evaporator 3 varies with the saturated vapor pressure of propylene in the evaporator. Since this saturated vapor pressure can be controlled by the operating pressure of the liquefied propylene 14 introduced into the evaporator 3, the vaporizing temperature may be set at an arbitrary level by adjusting the operating pressure of the liquefied propylene 14. The gasification of the liquefied propylene 14 requires the vaporizing temperature to be lowered below the temperature of the liquid coolant to be supplied, and this will inevitably entail the drop internal pressure, that is, the operating pressure of the evaporator. The drop of the operating pressure, however, results in increasing the specific volume of the gasified propylene and consequently requires the volume of the evaporator 3 itself to be enlarged for the purpose of retaining the rate of vaporization at a proper level in the evaporator 3. Specifically, when the temperature of the liquid coolant falls below 0° C., it becomes necessary to enlarge the volume of the evaporator 3 and, as a natural consequence, to enlarge the pipe lines through which the gasified propylene flows. During the stop of the operation or during an erroneous operation, the interior of the evaporator 3 is exposed to high pressure because the temperature of the propylene in the evaporator 3 rises to the same temperature as the liquid coolant to be supplied. The evaporator 3, therefore, must be designed with excessive pressure resist ability.

Conversely, when the temperature of the liquid coolant is high, the volume of the evaporator 3 may be reduced due to the rise of operating pressure in compliance with the above mentioned theory and practice. When the liquefied propylene 14 is supplied to the evaporator 3 by the inner pressure of the liquefied propylene storage tank (not shown), namely by the pressure of its own, since the inner pressure of the storage tank varies due to the ambient temperature, it becomes difficult to supply liquefied propylene by the pressure of its own, and is, therefore will be necessary to provide the high discharge pressure feed pump (not shown). Particularly, when the temperature of the liquid coolant is high in the case of an erroneous operation, the pressure in the evaporator 3 will rise abnormally. Specifically, when the temperature of the liquid coolant exceeds 50° C., the design pressure of evaporator 3 and the piping connected thereto should be raised similarly to the conventional use of steam. This invention, by setting the temperature of the liquid coolant in the aforementioned range, 0-50° C., in consideration of the facts mentioned above, enables the evaporator 3 and the pipe lines connected thereto to lower the design pressure and the ability to resist pressure, to reduce their sizes, and to acquire excellent effects.

The temperature of the chilled coolant to be obtained varies due to the flow amount of the liquid coolant introduced per unit time into the evaporator 3 and/or the flow volume of the liquefied propylene and/or propane 14 introduced per unit time into the evaporator 3. This invention, however, prefers to use the liquid coolant satisfying the specified ranges mentioned above and obtain the chilled coolant having the temperature in the range of –10-40° C., preferably –5-35° C., and particularly preferably 0-35° C. To obtain the chilled coolant having the temperature below –10° C., it is necessary to decrease the amount of the liquid coolant and it is difficult to prepare the chilled coolant to be circulated to the heat exchangers which is used in the process for producing acrylic acid. If the temperature of the chilled coolant exceeds 40° C., the amount of liquid coolant to be obtained will increase excessively and this will result in the deterioration of the efficiency of the process due to the requirement of further cooling of the chilled coolant in order to make it appropriate to use in whichever of the heat exchangers operated in the process for producing acrylic acid. The vaporizing pressure of the evaporator 3 is preferred to be in the range of 0.2-2 MPa in gauge pressure.

This invention may attain the purpose of setting the temperature of the liquid coolant at a level in the aforementioned range by providing the liquid coolant supplying system 1 with the liquid coolant thermocontroller 23 and supplying the liquid coolant having the temperature thereof adjusted to the range mentioned above. Further, for the purpose of adjusting the temperature of the liquid coolant and the amount of the liquid coolant to be supplied to the evaporator 3, the pressure controller 24 or the gas flow rate controller 25 may be installed between the evaporator 3 and the reactor 4.

In this invention, the chilled coolant which is obtained from the liquid coolant by heat exchange as described above may be used as the liquid coolant in other heat exchangers as it is. In case the chilled coolant is passed through the line 2 and further cooled by the refrigerator 13, the result will become preferable so that the chilled coolant will have a temperature which is appropriate to use in other heat exchangers. When the temperature of the chilled coolant is high, the liquid coolant thermocontroller 26 may be installed at the refrigerator 13 additionally to adjust the temperature of the chilled coolant. The reason for this additional installation is that the adjustment of the temperature consequently attained results in stabilizing the cooling and the condensation in the heat exchangers serving the purpose of supplying the chilled coolant.

In this invention, the chilled coolant having the temperature thereof adjusted by the refrigerator 13 is used as the liquid coolant for at least one of the heat exchangers attached to the plant for producing acrylic acid. These heat exchangers include the absorbing solvent cooler 8 attached to the acrylic acid absorbing column 5, the circulation cooler attached to the acrylic acid absorbing column, the condenser 10 attached to the solvent separating column 6 and the condenser 11 attached to the refining column 7, for example.

The refrigerator 13, for example, supplies the chilled coolant via the line 3 to the absorbing solvent cooler 8 which is attached to the acrylic acid absorbing column 5. Since the temperature of the absorbing solvent is preferred to be low for the purpose of high efficiency of acrylic acid absorption, the absorbing solvent is generally cooled in the heat exchanger before it is supplied to the acrylic acid absorbing column 5 and the liquid coolant for this cooling is introduced from another cooling system. In this invention, the power consumed for cooling can be decreased by using the chilled coolant mentioned above as the liquid coolant to be circulated to the cooler 8. When the chilled coolant is circulated to the cooler 8, the temperature thereof is properly in the range of 0-35° C., preferably in the range of 5-30° C. In order to prepare the chilled coolant which has appropriate temperature as mentioned above, it is preferable to install the liquid coolant thermocontroller 26 as stated above.

The absorbing column 5 is generally provided with the circulation cooler 9 for cooling a part of the heat entrained by the acrylic acid-containing gas supplied from the reactor 4 and enabled consequently to put to circulation part of the bottom of the column and, at the same time, supply the cooled acrylic acid absorbing solvent 21 from the top of the column, with the result that the temperature of the top of the column and the efficiency of acrylic acid absorption will be maintained at respectively prescribed levels. As the liquid coolant used in the circulation cooler 9, this invention allows use of the chilled coolant prepared as described above. Incidentally, the temperature of the chilled coolant prepared in the evaporator and/or adjusted by the liquid coolant thermocontroller is not always required to be equal to the temperature of the chilled coolant which is supplied to the coolers 8 and 9, etc. The chilled coolant to be circulated to the circulation cooler 9, for example, does not need to be limited to the chilled coolant which is cooled by the refrigerator 13. The chilled coolant withdrawn via the branch from the line 2 extending from the evaporator 3 through the refrigerator 13 may be used instead. When the chilled coolant is circulated to the circulation cooler 9, the temperature thereof is properly in the range of 0-40° C., preferably 5-35° C. The chilled coolant which has undergone heat exchange in the circulation cooler 9 is introduced via the line 5 and the chilled coolant which has undergone heat exchange in the cooler 8 is introduced via the line 4 and they are mixed. It is preferable to mix the chilled coolant which has different temperature and to return to resultant mixed chilled coolant to the liquid coolant supply system 1 via the line 6 and reuse as liquid coolant.

The chilled coolant emanating from the refrigerator 13 can be advanced through the branch from the line 3 and circulated to the condenser 10 attached to the solvent separating column 6 and used therein as the liquid coolant for heat exchange. As the chilled coolant to be used for this purpose, that which has been cooled by the refrigerator 13 proves favorable. When the chilled coolant is circulated to the condenser 10, the temperature thereof is properly in the range of 0-35° C., preferably 5-30° C. Incidentally, in order to prepare the chilled coolant which has appropriate temperature as mentioned above, the condenser 10 may be provided with the thermocontroller. The chilled coolant which has undergone heat exchange may be advanced from the condenser 10 through the line 7 and joined to the flow in the line 6, again returned to the liquid coolant supplying system 1 and reused as the liquid coolant.

The process for producing acrylic acid usually involves the acrylic acid refining column 7 in addition to the acrylic acid absorbing column and the solvent separating column mentioned above. When the acrylic acid refining column 7 is involved in the process, the chilled coolant mentioned above may be used as the liquid coolant for the heat exchanger attached to the acrylic acid refining column 7 such as, for example, the condenser 11 attached to the refining column. When the chilled coolant is circulated to such a heat exchanger, the temperature thereof is properly in the range of 20-35° C., preferably 20-30° C. The vapor of acrylic acid is distilled from the acrylic acid refining column 7 through the top thereof and subsequently cooled by the condenser 11 attached to the refining column to obtain acrylic acid. Meanwhile, the liquid 19 containing the by-product is recovered through the bottom of the column. Incidentally, the liquid coolant which has utilized in the condenser 10 attached to the solvent separation column or the condenser 11 attached to the refining column is passed through the line 7 and the line 8 and mixed with the flow through the line 6 and returned to the liquid coolant supplying system 1 and reused as the liquid coolant. When the apparatus for the production of acrylic acid mentioned above is connected to the methacrylic acid and/or (meth)acrylic esters plants 12, the liquid coolant mentioned above may be supplied as the liquid coolant for heat exchange in the plant 12 and the liquid coolant which has undergone this heat exchange advanced through the line 9, combined with the flow through the line and returned again to the liquid coolant supplying system 1 and reused as the liquid coolant.

One example of the chilled coolant used in the process for producing acrylic acid by the series of operations resorting to the reactor 4, acrylic acid absorbing column 5, solvent separating column 6, and refining column 7 has been installed. This invention allows the chilled coolant to be used in such heat exchangers installed in the plants other than the plant for producing acrylic acid and the plants further connected to the acrylic acid plant such as, for example, the methacrylic acid and/or (meth)acrylic esters plants 12. When the amount of the heat of the chilled coolant calculated from the amount of the chilled coolant obtained by gasification is in excess of the total amount of the heat required for cooling in the heat exchangers attached to the process for producing acrylic acid, when the amount of the heat of chilled coolant is in excess amount because the chilled coolant has been further cooled by the refrigerator 13, and when the chilled coolant usable for cooling is in excess amount because it has been used only in a part of the heat exchangers involved in the process for producing acrylic acid, these excess of the chilled coolant can be effectively utilized in the plants mentioned above instead of being wasted. Moreover, the use of the chilled coolant results in not only reduction of energy consumption for cooling but also stabilizing the process of production by effective utilization of the latent heat generated by the gasification of propylene. For example, part of the chilled coolant from the line 3 can be circulated to and used in the heat exchangers attached to the methacrylic acid and/or (meth)acrylic esters plants 12. The chilled coolant which has undergone heat exchange in this plant may be advanced through the line 9 and mixed with the flow through the line 6. Particularly, when the acrylic acid is further esterified to produce the acrylic esters, the chilled coolant supplied to and used in the heat exchangers incorporated in the apparatus for producing esters brings about the advantage of simplifying the installation of piping for the transfer of the chilled coolant.

Incidentally, when the acrylic acid absorbing column 5, solvent separating column 6, refining column 7, etc. are present in plural quantities or when plural coolers are connected to one acrylic acid absorbing column, for example, the chilled coolant may be supplied to any or all of the relevant units.

Further, this invention may discard the chilled coolant after it has been used for heat exchange and it nevertheless is preferred to have chilled coolants of different temperature levels to be combined and returned to and reused in the liquid coolant supplying system 1 attached to the cooling tower, for example. The discard of the chilled coolant in a large volume is unfavorable from the environmental preservation and economical point of view. This invention is also excellent in being capable of contributing to the preservation of environment owing to the cyclical use of the liquid coolant. The chilled coolant which is circulated to the liquid coolant supplying system 1 may be supplied via the line to the group of liquid coolant using devices 29 and used therein and, after being used therein, forwarded via the line 10 and combined with the flow in the line 6 and circulated to the liquid coolant supplying system 1.

Now, the supply route for the propylene and/or propane emanating from the evaporator 3 will be described. The propylene, for example, which has been gasified by the evaporator 3 is mixed with the inert gas and/or air through the inert gas supply route and the air supply route which are omitted from illustration herein and the reactant gas consequently formed is supplied to the reactor 4. Further, this invention can adjust the amount of the propylene and/or propane 14 to be gasified by properly controlling the amount of the liquid coolant introduced into the evaporator 3 as described above. That is, this invention can stabilize conversion and the yield in the step for producing acrylic acid by adjusting the amount of the liquid coolant to be introduced. The adjustment of the amount of the gasified propylene and/or propane supplied from the evaporator 3 and introduced into the reactor 4 may be attained by adjusting the gas flow rate using gas flow rate controller 25 installed in the line.

In the present invention, the reaction of catalytic gas phase oxidation of propylene with molecular oxygen containing gas can be carried out under the conditions adopted by the heretofore known method. In the case of propylene, for example, the reactant gas used for the reaction has appropriate propylene concentration in the range of 3-15 vol. %, the ratio of molecular oxygen containing gas to propylene in the range of 1-3, and comprises nitrogen, steam, carbon oxides, and propane, etc.

As the source for the molecular oxygen containing gas, air is advantageously used. Oxygen-enriched air and purified oxygen, optionally, may be used instead. This source is supplied by the one-pass mode or the recycling mode. Commendably, the reaction temperature is in the range of 250° C.-450° C., the reaction pressure in the range of absolute pressure 0.1-0.5 MPa, and the space velocity in the range of 500-3000 $h^{-1}$ (STP).

Though the reactor 4 does not need to be particularly discriminated on account of the kind, the shell-and-tube type reactor may be preferably used because it is effective for heat exchange.

As the catalyst with which the reactor 4 is to be packed for the production of acrylic acid by two-stage catalytic gas phase oxidation reaction, the oxidation catalyst which is generally used for the production of acrolein by the gas phase oxidation reaction of reactant gas can be used as the former-stage catalyst. By the same token, the latter-stage catalyst does not need to be particularly discriminated. The oxidizing catalyst which is generally used in the production of acrylic acid by the gas phase oxidation of the reaction gas mainly containing the acrolein obtained by the former stage in the method of the two-stage catalytic gas phase oxidation can be used, for example.

As concrete examples of the former-stage catalyst, the compositions represented by the general formula, $Mo_a—Bi_b-Fe_c-A_d-B_e—C_f-D_g-O_x$ (wherein Mo, Bi, and Fe respectively denote molybdenum, bismuth, and iron, A denotes at least one element selected from the group consisting of nickel and cobalt, B denotes at least one element selected from the group consisting of alkali metals and thallium, C denotes at least one element selected from the group consisting of phosphorus, niobium, manganese, cerium, tellurium, tungsten, antimony, and lead, D denotes at least one element selected from the group consisting of silicon, aluminum, zirconium, and titanium, and O denotes oxygen, and a, b, c, d, e, f, g, and x respectively denote the atomic ratios of Mo, Bi, Fe, A, B, C, D and O which fall respectively in b=0.1-10, c=0.1-10, d=2-20, e=0.001-5, f=0-5, and g=0-30 when a=12 is fixed, and x denotes the value determined by the states of oxidation of the relevant elements) may be cited.

As concrete examples of the latter-stage catalyst, the compositions represented by the general formula, $Mo_a—V_b—W_c—Cu_d-A_e-B_f—C_g—O_x$ (wherein Mo denotes molybdenum, V denotes vanadium, W denotes tungsten, Cu denotes copper, A denotes at least one element selected from the group consisting of antimony, bismuth, tin, niobium, cobalt, iron, nickel, and chromium, B denotes at least one element selected from the group consisting of alkali metals, alkaline earth metals, and thallium, C denotes at least one element selected from the group consisting of silicon, aluminum, zirconium, and cerium, and O denotes oxygen, a, b, c, d, e, f, g, and x respectively denote the atomic ratios of Mo, V, W, Cu, A, B, C, and O which fall in the ranges of b=2-14, c=0-12, d=0.1-5, e=0-5, f=0-5, and g=0-20 when a=12 is fixed, and x denotes the value determined by the states of oxidation of the relevant elements) may be cited.

The catalyst does not need particularly to discriminate the shape thereof but may be in the shape of spheres, circular columns, cylinders, etc. It may be formed by such methods as carrier molding, extrusion molding, and tablet molding. The catalyst of the type having a catalytic substance deposited on a refractory carrier is particularly useful.

The production of the acrylic acid is accomplished by introducing the reactant gas under the conditions mentioned above into the former-stage catalyst layer and then introducing the formed gas mainly containing acrolein either directly or after having added air and steam into the latter-stage catalyst layer.

Specifically, for the purpose of forming the acrylic acid, the reaction tubes in the reactor 4 are packed with the oxide catalyst (latter-stage catalyst) and the acrolein-containing gas obtained by the former-stage reaction or the mixed gas prepared, when necessary, by adding air, oxygen, or steam to the gas is supplied to the reaction tubes at the reaction temperature (the temperature of the catalyst in the reactor) in the range of 100-380° C., preferably 150-350° C., and the space velocity in the range of 300-5,000 $hr^{-1}$ (STP) and subjected to the latter-stage reaction to produce the acrylic acid.

Incidentally, the formation of the acrolein-containing gas does not need to be limited to such two-stage reaction of catalytic gas phase oxidation as described above but may be attained by using different reactors respectively for the two stages involved and performing the reactions in two or more stages. In this case, the acrolein-containing gas is formed by one-stage reaction of catalytic gas phase oxidation. Similarly, propane may be used in the place of propylene and the latent heat may be recovered and utilized as in an apparatus for producing acrylic acid.

The reactor 4 generates a great deal of heat of reaction. As the heat medium for circulation in the reactor for the purpose of removing this heat of reaction, any of the heat medium heretofore known to the art may be used. As concrete examples of the heat medium for circulation in the reactor, molten salts, niter, and phenyl ether type heat medium which is the Dowtherm type organic heat medium may be cited. The reactor heat medium which has the temperature thereof elevated by removing the heat of the reaction tubes is cooled in the heat exchanger attached to the reactor.

Then, the acrylic acid-containing gas 20 emanating from the reactor 4 is supplied to the acrylic acid absorbing column 5. In the absorbing column 5, the absorbing solvent 21 is supplied thereto via the absorbing solvent cooler 8 and utilized therein to prepare the acrylic acid-containing solution. The waste gas 20 emanating from the top of the absorbing column 5 is either discarded or recycled. By using the cooled acrylic acid absorbing solvent 21, it makes possible to improve the efficiency of acrylic acid absorption in the acrylic acid absorbing column 5.

The absorbing solvent 21 in the absorbing column 5 may be used any of the known absorbing solvents such as, for example, water, organic acid-containing waters, and the solvents which have high boiling point such as inactive hydrophobic organic solvents (represented by diphenyl ether and diphenyls). When water is used as absorbing solvent 21, for example, the aqueous acrylic acid solution to be obtained from the acrylic acid absorbing column 5 under the generally employed conditions for the production of acrylic acid generally contains acrylic acid in the range of 50-80 mass %, acetic acid in the range of 1-5 mass %, and water in the range of 20-40 mass %. These concentration are varied by the operating conditions of the oxidation reaction in the reactor or the absorbing column. Incidentally, the temperature at the top of the acrylic acid absorbing column is preferred to be in the range of 40-70° C.

Subsequently, the acrylic acid-containing solution is supplied to the solvent separating column 6 and separated therein into acrylic acid and the solvent. The distillate emanating from this column from the top thereof is condensed and cooled by the condenser 10 attached to the column. In case the solvent which has lower boiling point than acrylic acid such as water is used as the absorbing solvent, the acrylic acid is withdrawn through the bottom of the column. In case the solvent has higher boiling point mentioned above, the acrylic acid is withdrawn through the middle of the column. In any cases, the column can be operated under the heretofore known conditions to be employed when such solvents are used. Even when the solvent separating column is required to be followed by an acrylic acid refining column in the sequence of process for the purpose of obtaining acrylic acid as a product, the operation of the refining column may be performed under the conditions heretofore known to the art.

Figure 3:
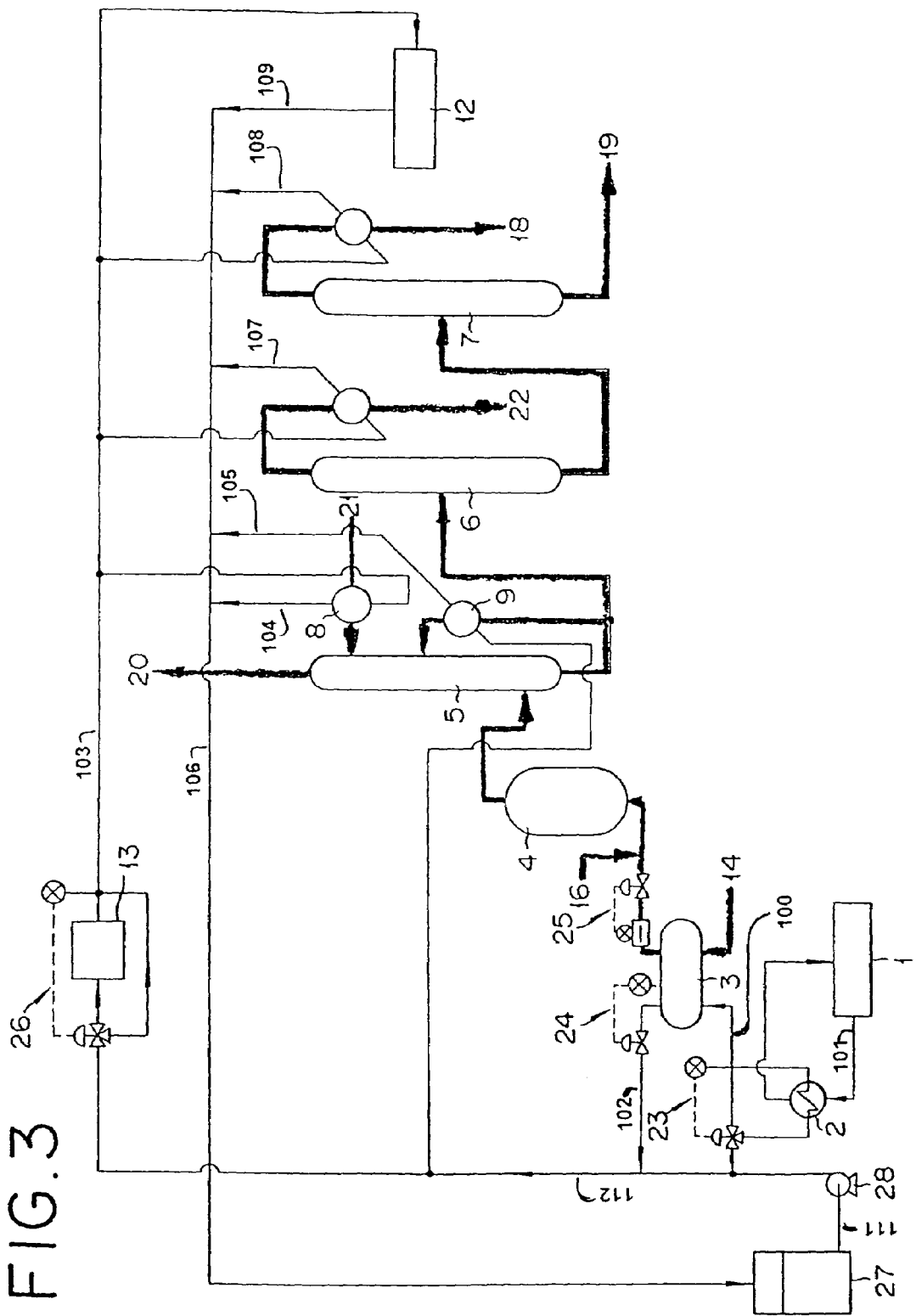
FIG. 3 is a diagram illustrating a preferred working example of this invention for producing acrylic acid by using brine as the liquid coolant.

When the refining column is required, this column is additionally provided with the condenser 11 which fulfills the function of condensing and cooling the distillate emanating from the top of the column. As the liquid coolant used in this condenser 11, the chilled coolant which is prepared by the gasification mentioned above may be used. The liquid coolant which has been used in the condenser 11 as described above may be circulated to the liquid coolant supplying system 1. Incidentally, FIGS. 2 and 3 depict the processes which use the solvent having a lower boiling point than acrylic acid as the acrylic acid absorbing solvent and recover the acrylic acid-containing solution through the bottom of the solvent separating column 6.

The method for the production of acrylic acid which includes the steps for producing acrylic acid by absorbing acrylic acid by using the solvent having high boiling point and subjecting the acrylic acid obtained from the solvent separating column 6 to further refinement and a step for obtaining gasified propylene and/or propane by means of at least a evaporator answers the designation "method for the production of acrylic acid" as used in the specification of this invention even when the chilled coolant to be obtained is used for heat exchange. The method for the production of acrylic acid contemplated by this invention, therefore, is not limited to the case of simply producing acrylic acid but is inclusive of the case which includes steps branching into the steps for producing an acrylic esters.

In the case of including the process for producing acrylic esters from acrylic acid as described above, the acrylic acid is withdrawn such as from the solvent separating column 6 through the bottom thereof, transferred to the step for esterifying acrylic acid, and used in its unmodified form as the raw material for producing the acrylic esters. This step for producing the acrylic esters includes steps for light ends separation, heavy ends separation and refining of the acrylic esters. Generally, apparatus in these steps are each attached with coolers and condensers to effect heat exchange. This invention allows the chilled coolant prepared by the gasification mentioned above to be used for the purpose of such heat exchange as mentioned above.

Now, the case of producing acrylic acid by using brine as the liquid coolant will be described below with reference to FIG. 3. FIG. 3 shares the same reference numerals and line symbols with FIG. 2.

The brine to be used as the liquid coolant is transferred from the liquid coolant tank 27 through the line 11 to the liquid coolant heater 2 by means of the liquid coolant transfer pump 28. When the liquid coolant tank 27 is additionally provided with the liquid coolant thermocontroller 23, liquid coolant heater 2 which is provided in part of the line 11 is no longer required. Particularly, however, the brine is capable of retaining the lower temperature than water. In case the apparatus which produces (meth)acrylic acid and/or (meth)acrylic ester and involves cyclic use of the chilled coolant, for example, has part thereof suspended from operation, there are cases where the temperature of the liquid coolant falls to extremely low level. In this case, therefore, it is preferable to make the liquid coolant temperature controlled in the range of 0-50° C. by using the liquid coolant heater 2 and then introduce it into the evaporator 3 through the line 1-1. When the brine is used, for example, by supplying brine having an ethylene glycol concentration of 30 mass % at the temperature in the range of 0-30° C. to the evaporator 3, it makes possible to obtain the chilled coolant having the temperature in the range of −5-25° C.

When the plant is provided with lines so installed that the chilled coolant used in any of the heat exchangers incorporated in the plant may be recovered in the liquid coolant tank 27, it makes possible to store the used chilled coolant in the liquid coolant tank 27 and transfer the liquid coolant from the tank using the liquid coolant transfer pump 28 which is installed in the line 11 connected to the tank. When the liquid coolant tank 27 is disposed as described above, the pressure accumulating in the line for the liquid coolant transfer and the non-condensable gas possibly leaking in a minute amount into the liquid coolant may be separated. Particularly since the brine can be a chilled coolant of a lower temperature than water, the liquid coolant may be circulated only partly to the evaporator 3 and used as the chilled coolant instead of being wholly circulated to the evaporator 3. For example, part of the liquid coolant flowing from the liquid coolant transfer pump 28 through the line 11 is circulated to and cooled in the evaporator 3, forwarded via the line 2 which is the line of the chilled coolant to the evaporator 3, and combined with the flow through the line 11. The chilled coolant which has been obtained by being cooled as described above has a temperature different from the temperature of the liquid coolant flowing through the line 11 and the line 2. When the line 12 is laid subsequently to the point of confluence, the chilled coolant can be forwarded through the line 12 directly to the circulation cooler 9 attached to the acrylic acid absorbing column and used therein as the chilled coolant. The chilled coolant may be transferred through the line 12 to the refrigerator 13, further cooled therein, and thereafter forwarded to the circulation cooler 9 attached to the acrylic acid absorbing column and used as the chilled coolant therein.

The propylene which has been gasified by the evaporator 3 is supplied to the reactor 4. From this point forward, the circulation and use of the chilled coolant and the supply of the reactant gas to the reactor are the same as those depicted in FIG. 2.

FIG. 3 depicts the case of using brine as the liquid coolant and additionally providing the liquid coolant tank 27, for example. The construction of FIG. 3 permits use of water as the liquid coolant. Similarly, the construction of FIG. 2 permits use of brine as the liquid coolant.

The second aspect of this invention consists in An apparatus for the production of acrylic acid or acrolein, comprising means for gasifying liquefied propylene and/or propane introduced into an evaporator by supplying a liquid coolant to said evaporator and, at the same time, preparing a chilled coolant by recovering the latent heat of the liquefied propylene and/or propane, means for subjecting the resultant gasified propylene and/or propane to a catalytic gas phase oxidation reaction thereby preparing a gas containing acrylic acid or acrolein, and means for using said chilled coolant in heat exchangers attached to the apparatus for the production of acrylic acid or acrolein.

The acrylic acid is produced through acrolein by the reaction of catalytic gas phase oxidation of propylene and/or propane. The apparatus for production according this invention recovers the latent heat of liquefied propylene and/or propane and stabilize the process for producing acrylic acid or acrolein as well and, consequently, produces acrylic acid of high quality and decreases the amount of electric energy consumed for cooling in the equipments, for examples, heat exchangers of the process of the production.

In the apparatus of this invention, as the "means for gasifying liquefied propylene and/or propane introduced into the evaporator by supplying the liquid coolant to the evaporator and, at the same time, preparing the chilled coolant by recovering the latent heat of the liquefied propylene and/or propane," the evaporator 3 which is illustrated in FIG. 2 and FIG. 3 may be cited. When the pipe line for liquefied propylene in the evaporator 3 is supplied with propylene and, at the same time, the liquid coolant is introduced into the interior of the evaporator 3 incorporating the pipe line, heat exchange proceeds between the propylene and the liquid coolant, with the result that the liquid coolant will be cooled by recovering the latent heat generated in consequence of the gasification of the liquefied propylene and consequently enabled to prepare the chilled coolant. The means for preparing the chilled coolant may be provided with the liquid coolant supplying system 1 for storing the liquid coolant, the heater for heating the liquid coolant to the appropriate temperature which suits to the gasification, and the liquid coolant thermocontroller 23 for measuring the temperature of the liquid coolant and then adjusting the liquid coolant to the appropriate temperature which suits to supply the liquid coolant to the evaporator 3 as accessorial devices for converting the liquid coolant into the chilled coolant through exchange of heat.

Then, as the "means for subjecting the gasified propylene and/or propane to a reaction for catalytic gas phase oxidation thereby preparing the gas containing acrylic acid or acrolein," the reactor 4 for catalytic gas phase oxidation may be cited. The kind of the reactor 4 and the conditions for the use thereof can be applied kinds and conditions in the prior art for the production of acrylic acid.

As the "means for using the chilled coolant in heat exchangers attached to the apparatus for producing acrylic acid or acrolein," the piping connected from the evaporator 3 to various heat exchangers, the lines 2, 3, and 11, and various heat exchangers may be cited. The pipe lines may include temperature adjusting means such as the liquid coolant thermocontroller 26 for the chilled coolant and the gas flow rate controller 25 as means for flow rate adjustment and they may be additionally provided with the refrigerator 13 for further cooling the chilled coolant and the liquid coolant thermocontroller 26.

The apparatus for production according to this invention can include "means for circulating the chilled coolant used in the heat exchangers to means for preparing the chilled coolant." As concrete examples of this circulating means, the pipe lines for circulating the chilled coolant circulated to the heat exchangers to the liquid coolant supplying system 1, namely the lines 4, 5, 6, 7, 8, 9, and 11. These pipe lines may be additionally provided with the liquid coolant transfer pump 28.

This invention effectively utilizes the latent heat which used to be discarded and consequently enables the energy consumption for cooling to be reduced. It, therefore, obviates the necessity for the power line distribution heretofore indispensable in the operation of various heat exchangers.

EXAMPLES

Now, this invention will be described more specifically below with reference to working examples.

(Example of Production of Catalyst)

In 150 liters of purified water kept heated and stirred, 100 kg of ammonium molybdate and 6.3 kg of ammonium paratungstate were dissolved. To this solution, an aqueous nitrate solution separately prepared by mixing of solution of 55 kg of cobalt nitrate in 100 liters of purified water, a solution of 19 kg of ferric nitrate in 30 liters of purified water, and a solution of 22.9 kg of bismuth nitrate in 30 liters of purified water incorporating 6 liters of concentrated nitric acid was added dropwise. A solution of 14.2 kg of an aqueous 20 mass % silica sol solution and 0.29 kg of potassium nitrate in 15 liters of purified water was continuously added thereto. The suspension thus obtained was heated under stirring, evaporated to driness, and then dried and pulverized. The produced powder was formed in cylinders 5 mm in diameter and calcined under stream of air at 460° C. for six hours to afford a catalyst.

Example 1

Acrylic acid was produced by using the apparatus for the production illustrated in FIG. 2. First, from the liquid coolant supplying system 1, water which temperature had been adjusted at 30° C. by the liquid coolant thermocontroller 23 was supplied in the flow amount of 70 m³/h to the propylene evaporator 3. Liquefied propylene was supplied meantime at the flow amount of 2500 kg/h to the evaporator 3. The vaporizing pressure of the propylene was 0.6 MPa in gauge pressure. As a result, the chilled coolant having the temperature of 27° C. was obtained at the flow amount of 70 m³/h. This chilled coolant was further cooled up to 20° C. by using refrigerator 13.

This chilled coolant was circulated to and used in absorbing solvent cooler 8, the condenser 10 attached to the solvent separating column, and the condenser 11 attached to the refining column. The used chilled coolant was introduced to the liquid coolant supplying system 1 and reused as liquid coolant. To the circulation cooler 9 attached to the acrylic acid absorbing column, the chilled coolant having the temperature of 27° C. was directly supplied through the line 2.

The reaction tubes in the reactor 4 for catalytic gas phase oxidation were packed with 5.6 m³ of the catalyst (composition: Mo: 12, Bi: 1, Fe: 1, Co: 4, W: 0.5, Si: 1, and K: 0.06 in molar ratio) obtained in the example of production. The reactant gas was composed of 6 vol. % of propylene, 12 vol. % of oxygen, 9 vol. % of steam, and 73 vol. % of nitrogen, etc. The reactant gas was introduced so as to acquire the retention time of 2 seconds on the catalyst. The results were as shown below.

Fluctuation of pressure of propylene gas in the evaporator: Not more than ±2 kPa Power consumption in refrigerator: 467 MWh/Y Efficiency of absorption of acrylic acid immediately after start of operation: 99.5%

Efficiency of absorption of acrylic acid after six months' operation: 99.4%

Efficiency of absorption of acrylic acid after one year's operation: 99.2%

Number of suspensions of apparatus due to the polymerization: 0/year

Comparative Example 1

Acrylic acid was produced by following the procedure of Example 1 while supplying saturated steam having the temperature of 120° C. and the gauge pressure of 0.1 MPa at the flow volume of 390 kg/h instead of the liquid coolant to the propylene evaporator 3, discarding the steam after heat exchange without deriving any chilled coolant therefrom, and obtaining the heat source for heat exchange in the attached devices wholly from the liquid coolant supplying system and the refrigerator. The vapor pressure of propylene was 1.0 MPa in gauge pressure. The results were as shown below.

Fluctuation of pressure of propylene gas in evaporator: Not more than ±10-20 kPa Power consumption in refrigerator: 937 MWh/Y Efficiency of absorption of acrylic acid immediately after start of operation: 99.5%

Efficiency of absorption of acrylic acid after six months' operation: 97.2%

Efficiency of absorption of acrylic acid after one year's operation: Unmeasurable Number of suspensions of apparatus due to the polymerization: 2/year

Example 2

Acrylic acid was produced by using the apparatus for the production illustrated in FIG. 3. First, from the liquid coolant supplying system 1, brine (aqueous 30 mass % ethylene glycol solution) had been adjusted to the temperature of 12° C. by the liquid coolant thermocontroller 23 was supplied at the flow amount of 120 m³/h to the propylene evaporator 3. The vapor pressure of propylene was 0.4 MPa in gauge pressure. Liquefied propylene was supplied meantime at the flow amount of 4200 kg/h to the evaporator 3. As a result, the chilled coolant having the temperature of 9° C. was obtained at the flow amount of 120 m³/h. This chilled coolant was combined with the liquid coolant from the liquid coolant supplying system 1 and then cooled up to 8° C. by using refrigerator 13.

This chilled coolant was circulated to and used in the same manner as in Example 1 while omitting the circulation thereof to the condenser 11 attached to the refining column.

The reaction tubes in the reactor 4 for catalytic gas phase oxidation were packed with 5.6 m³ of the catalyst (composition: Mo: 12, Bi: 1, Fe: 1, Co: 4, W: 0.5, Si: 1, and K: 0.06 in molar ratio) obtained in the example of production. The reactant gas was composed of 6 vol. % of propylene, 12 vol. % of oxygen, 9 vol. % of steam, and 73 vol. % of nitrogen, etc. The reactant gas was introduced so as to acquire the retention time of 2 seconds on the catalyst. The results were as shown below.

Fluctuation of pressure of propylene gas in evaporator: Not more than ±2 kPa

Power consumption in refrigerator: 3063 MWh/Y

Efficiency of absorption of acrylic acid immediately after start of operation: 99.6%

Efficiency of absorption of acrylic acid after six months' operation: 99.4%

Efficiency of absorption of acrylic acid after one year's operation: 99.3%

Number of suspensions of apparatus due to the polymerization: 0/year

Comparative Example 2

Acrylic acid was produced by following the procedure of Example 2 while supplying saturated steam having the temperature of 120° C. and the gauge pressure of 0.1 MPa at the flow volume of 650 kg/h instead of the liquid coolant to the propylene evaporator 3, discarding the steam after heat exchange without deriving any chilled coolant therefrom, and obtaining the heat source for heat exchange in the attached devices wholly from the liquid coolant supplying system and the refrigerator. The vapor pressure of propylene was 1.0 MPa in gauge pressure. The results were as shown below.

Fluctuation of pressure of propylene gas in evaporator: Not more than ±10-20 kPa Power consumption in refrigerator: 3835 MWh/Y Efficiency of absorption of acrylic acid immediately after start of operation: 99.4%

Efficiency of absorption of acrylic acid after six months' operation: 97.0%

Efficiency of absorption of acrylic acid after one year's operation: Unmeasurable Number of suspensions of apparatus due to the polymerization: 2/year (Results)

(1) In Comparative Example 1, the fluctuation of the pressure of propylene gas in the evaporator was not more than ±10-20 kPa of the set value. In Example 1, the variation was not more than ±2 kPa of the set value.

(2) When the refrigerators used in Example 1 and Comparative Example 1 were tested for power consumption, the power consumption in Example 1 was found to be 467 MWh/Y and that in Comparative Example 1 to be 937 MWh/Y. The difference was 470 MWh/Y.

(3) When the refrigerators used in Example 2 and Comparative Example 2 were tested for power consumption, the power consumption in Example 2 was found to be 3063 MWh/Y and that in Comparative Example 1 to be 3835 MWh/Y. The difference was 772 MWh/Y.

(4) In Comparative Examples 1 and 2, the efficiency of absorption of acrylic acid in the absorbing column which was 99.5% during the initial stage of operation fell to 97% after the elapse of six months. In Examples 1 and 2, the efficiency of absorption of acrylic acid in the absorbing column was maintained at 99.0% even after the elapse of one year following the start of operation. As a result, the load on the solvent separating column was stabilized and the supply of the liquid coolant at the prescribed temperature to the condenser attached to the column was easily attained. Consequently, the load on the columns was stabilized and the liquid coolant was easily supplied to the heat exchangers. No suspension of the operation of the apparatus, therefore, was caused by polymerization as in the vacuum equipments attached to the columns.

The invention claimed:

1. A method for the production of acrylic acid or acrolein, comprising gasifying liquefied propylene and/or propane introduced into an evaporator by supplying a liquid coolant to the evaporator and, at the same time, preparing a chilled coolant by recovering the latent heat of the liquefied propylene and/or propane, subjecting the resultant gasified propane and/or propylene to a catalytic gas phase oxidation reaction thereby preparing a gas containing acrylic acid or acrolein, and using said chilled coolant in heat exchangers attached to the apparatus for the production acrylic acid or acrolein.

2. A method according to claim 1, wherein the temperature of said liquid coolant supplied to said evaporator is in the range of 0-50° C.

3. A method according to claim 1, wherein said liquid coolant is water or brine.

4. A method according to claim 1, where in said heat exchanger is at least one member selected from the group consisting of an absorbing solvent cooler and a circulation cooler attached to the acrylic acid absorbing column, a condenser attached to the solvent separating column, and a condenser attached to the acrylic acid refining column.

5. A method according to claim 1, wherein said chilled coolant is used in heat exchangers attached to a methacrylic acid and/or (meth)acrylic esters plant.

6. A method according to claim 1, wherein the chilled coolant which has been used in said heat exchangers is reused as a liquid coolant.

7. A method according to claim 1, wherein the amount of said liquefied propylene and/or propane to be gasified is adjusted by controlling the amount of said liquid coolant into the evaporator.

* * * * *